(12) United States Patent
Mukhopadhyay et al.

(10) Patent No.: US 6,410,029 B1
(45) Date of Patent: Jun. 25, 2002

(54) 2-METHOXYESTRADIOL-INDUCED APOPTOSIS IN CANCER CELLS

(75) Inventors: Tapas Mukhopadhyay; Jack A. Roth, both of Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/351,191

(22) Filed: Jul. 9, 1999

Related U.S. Application Data

(62) Division of application No. 08/688,613, filed on Jul. 30, 1996, now Pat. No. 5,958,892.

(51) Int. Cl.[7] .......................... A61K 39/00; C07K 1/00; C07K 14/00; C07K 17/00; A01N 43/04

(52) U.S. Cl. ..................... 424/198.1; 514/44; 530/350; 435/70.1; 435/325; 435/320.1; 435/455

(58) Field of Search ................................ 435/325, 455, 435/70.1, 320.1; 530/350; 424/198, 198.1; 514/44

(56) References Cited

U.S. PATENT DOCUMENTS

| | | | |
|---|---|---|---|
| 5,504,074 A | 4/1996 | D'Amato et al. | |
| 5,527,676 A | 6/1996 | Vogelstein et al. | 435/6 |
| 5,532,220 A | 7/1996 | Lee et al. | 514/44 |
| 5,643,900 A | 7/1997 | Fotsis et al. | 514/182 |

FOREIGN PATENT DOCUMENTS

| | | |
|---|---|---|
| EP | 0 390 323 A2 | 10/1990 |
| FR | 2688514 | 9/1993 |
| WO | WO 90/05180 | 5/1990 |
| WO | WO 91/15580 | 10/1991 |
| WO | WO 93/03769 | 3/1993 |
| WO | WO 94/10323 | 5/1994 |
| WO | WO 94/18992 | 9/1994 |
| WO | WO 94/24297 | 10/1994 |
| WO | WO 95/02697 | 1/1995 |
| WO | WO 95/14101 | 5/1995 |
| WO | WO 95/14102 | 5/1995 |
| WO | WO 95/23867 | 9/1995 |
| WO | WO 95/28948 | 11/1995 |

OTHER PUBLICATIONS

Fotsis et al, Nature, 1994, 368: 237–239.*

Aizu–Yokota et al., "Natural Estrogens Induce Modulation of Microtubules in Chinese Hamster V79 Cells in Culture," *Cancer Research*, 55: 1863–1868, May 1, 1995.

Baker et al., Chromosome 17 Deletions and p53 Gene Mutations in Colorectal Carcinomas, *Science*, 244:217–221, Apr. 1989.

Baker et al., "p53 Gene Mutations Occur in Combination with 17p Allelic Deletions as Late Events in Colorectal Tumorigenesis," *Cancer Research*, 50:7717–7722, Dec. 1990.

Baker et al., "Suppression of Human Colorectal Carcinoma Cell Growth by Wild–Type p53," *Science*, 249:912–915, Aug. 1990.

Carter et al., "Adenovirus Containing a Deletion of the Early Region 2A Gene Allows Growth of Adeno–Associated Virus with Decreased Efficiency," *Virology*, 191:473–476, 1992.

Casey et al., "Growth Suppression of Human Breast Cancer Cells by the Introduction of a Wild–Type p53 Gene," *Oncogene*, 6:1791–1797, 1991.

Cushman et al., "Synthesis, Antitubulin and Antimitotic Activity, and Cytotoxicity of Analogs of 2–Methoxyestradiol, and Endogenous Mammalian Metabolite of Estradiol That Inhibits Tubulin Polymerization by Binding to the Colchicine Binding Site," *Journal of Medicinal Chemistry*, 38: 2041–2049, 1995.

D'Amato et al., "2–Methoxyestradiol, and endogenous mammalian metabolite, inhibits tubulin polymerization by interacting at the colchicine site," *Proceedings of the National Academy of Science USA*, 91: 3964–3968, Apr. 1994.

Davidson et al., "A Model System for In Vivo Gene Transfer into the Central Nervous System Using an Adenoviral Vector," *Nature Genetics*, 3:219–223, Mar. 1993.

DeSombre et al., "Estrogen Receptor–Directed Radiotoxicity with Auger Electrons: Specificity and Mean Lethal Dose," 5752–5758.

Diller et al., "p53 Functions as a Cell Cycle Control Protein in Osteosarcomas," *Molecular and Cellular Biology*, 10(11):5772–5781, Nov. 1990.

Eliyahu et al., "Meth A Fibrosarcoma Cells Express Two Transforming Mutant p53 Species," *Oncogene*, 3:313–321, 1988.

Eliyahu et al., "p53—A Potential Suppressor Gene?" *Journal of Cellular Biochemistry*, UCLA Symposia on Molecular & Cellular Biology, Abstracts, 19th Annual Meeting, Supplement 14C:264, Abstract No. I 030, Feb. 3—Mar. 11, 1990.

Eliyahu et al., "Wild–Type p53 Can Inhibit Oncogene–Mediated Focus Formation," *Proc. Natl. Acad. Sci. USA*, 86:8763–8767, Nov. 1989.

Finlay et al., "The p53 Proto–Oncogene Can Act as a Suppressor of Transformation," *Cell*, 57:1083–1093, Jun. 1989.

(List continued on next page.)

*Primary Examiner*—Deborah Crouch
*Assistant Examiner*—Peter Paras, Jr.
(74) *Attorney, Agent, or Firm*—Fulbright & Jaworski, LLP

(57) ABSTRACT

The present invention details methods for the treatment of cancer. In particular, it concerns the induction of apoptosis of cancer cells following treatment with methoxyestradiol. 2-methoxyestradiol (2-MeOE$_2$) increase wild-type p53 levels in a human non-small lung cancer cell lines associated with accumulation of cyclin dependent kinase inhibitor p21 WAF1/CIP1. Significant apoptotic cell death occurred after the drug treatment. Thus, 2-MeOE$_2$ facilitates induction of p53-mediated apoptosis.

26 Claims, 3 Drawing Sheets

OTHER PUBLICATIONS

Gebhardt et al., "A Tumor Suppressor Proto–Oncogene p53 Can Block Progression Through the Cell Cycle," Association of American Physicians, American Society for Clinical Investigation, American Federation for Clinical Research, Subspecialty Meetings, Sheraton Washington Hotel, Washington, D.C., May 6, 1990, Abstract.

Graham and Prevec, "Manipulation of Adenovirus Vectors," *Methods in Molecular Biology, Gene Transfer and Expression Protocols*, E.J. Murray (ed.), The Humana Press, Inc., vol. 7, Chapter 11, pp. 109–128, 1991.

Hermeking et al., "p53 Mediates c–Myc–Induced Apoptosis," *Cell Biology International*, 19(8): 705–706, 1995.

Hinds et al., "Mutation is Required to Activate the p53 Gene for Cooperation with the ras Oncogene and Transformation," *Journal of Virology*, 63(2):739–746, Feb. 1989.

Hinds et al., "The p53 Proto–Oncogene Can Suppress Transformation by Other Oncogenes, and Mutations in the Proto–Oncogene Can Activate the Gene for Transformation," *Common Mechanisms of Transformation by Small DNA Tumor Viruses*, Chapter 7, pp. 83–101, 1989.

Hinds, "Biological Consequences of Mutation of the p53 Proto–Oncogene," *UMI Dissertation Services*, Oct. 1989.

Huang et al., "Suppression of the Neoplastic Phenotype by Replacement of the RB Gene in Human Cancer Cells," *Science*, 242–1563–1566, Dec. 1988.

Hughes et al., "Comparison of the Distribution of Radioiodinated–E–17α–Iodovinyl–11β–Methoxyestradiol and 2–Iodo–1, 1–bis(4–Hydroxyphentl)–Phenylethylene Estrogens in the Immature Female Rat," *Journal of Nuclear Medicine*, 34(2): 272–280, Feb. 1993.

Isola et al., "Association of Overexpression of Tumor Suppressor Protein p53 With Rapid Cell Proliferation and Poor Prognosis in Node–Negative Breast Cancer Patients," *Journal of the National Cancer Institute*, 84(14): 1109–1114, Jul. 15, 1992.

Kadkol et al., "Effect of Testosterone and 17β Estradiol an p53 and C–ERB B2 Genes in Human Prostatic Adenocarcinoma Cell Lines," *Clinical and Investigative Medicine*, 18(4) (Suppl), 1995, 3877, Abstract Only.

Klessig et al., "Introduction, Stable Integration, and Controlled Expression of a Chimeric Adenovirus Gene Whose Product is Toxic to the Recipient Human Cell," *Molecular and Cellular Biology*, 4(7):1354–1362, Jul. 1984.

Labrie et al., "Regulation of Cyclin Kinase Inhibitory protein Expression by Estradiol in Human Breast Cancer Cells," *Clinical and Investigative Medicine*, 18(4) (Suppl), 1995, 251, Abstract Only.

Lamb and Crawford, "Characterization of the Human p53 Gene," *Molecular and Cellular Biology*, 6(5):1379–1385, May 1986.

Lee et al., "Molecular Basis of Tumor Suppression by the Human Retinoblastoma Gene," *Journal of Cellular Biochemistry*, UCLA Symposia on Molecular & Cellular Biology, Abstracts, 19th Annual Meeting, Supplement 14C, Abstract No. I 001, Feb. 3—Mar. 11, 1990.

Levine et al., "The p53 Growth Suppressing Gene Can Inhibit Transformation by Other Oncogenes," *The Journal of Cell Biology*, The American Society for Cell Biology, Twenty–ninth Annual Meeting, Nov. 5–9, 1989, Houston, Texas, Abstracts, 1989.

Levine et al., "The p53 Growth Suppressor Gene," *Journal of Cellular Biochemistry*, UCLA Symposia on Molecular & Cellular Biology, Abstracts, 19th Annual Meeting, Supplement 14C:264, Abstract No. I 029, Feb. 3—Mar. 11, 1990.

Li and Trush, "Reactive Oxygen–dependent DNA Damage Resulting from the Oxidation of Phenolic Compounds by a Copper–Redox Cycle Mechanism," *Cancer Research*, (Suppl) 54: 1895s–898s, 1994.

Li et al., "Carcinogenic Activities of Various Steroidal and Nonsteroidal Estrogens in the Hamster Kidney: Relation to Hormonal Activity and Cell Proliferation," *Cancer Research*, 55: 4347–4351, 1995.

Lottering et al., "Effects of 17β–Estradiol Metabolites on Cell Cycle Events n MCF–7 Cells," *Cancer Research*, 52: 5926–5932, 1992.

Malkin et al., "Mutant p53 Confers Tumorignicity to a Cell Line Lacking p53: Evidence for a Second p53 Function in Tumor Formation," *Blood*, 76(10, Supp. 1):238a, 1990.

Mercer et al., "Antiproliferative Effects of Wild Type Human P53," *Journal of Cellular Biochemistry*, UCLA Symposia on Molecular & Cellular Biology, Abstracts, 19th Annual Meeting, Supplement 14C:264, Abstract No. I 224, Feb. 3—Mar. 11, 1990.

Minna et al., "The Molecular Pathogenesis of Lung Cancer Involves the Accumulation of a Large Number of Mutations in Dominant Oncogenes and Multiple Tumor Suppressor Genes (Recessive Oncogenes)," *Journal of Cellular Biochemistry*, UCLA Symposia on Molecular & Cellular Biology, Abstracts, 19th Annual Meeting, Supplement 14C:264, Abstract No. I 003, Feb. 3—Mar. 11, 1990.

Napolitano et al., "11β–Substituted Estradiol Derivatives, Potential High–Affinity Carbon–11–Labeled Probes for the Estrogen Receptor: A Structure–Affinity Relationship Study," *Journal of Medicinal Chemistry*, 38: 429–434, 1995.

Prevec et al., "Use of Human Adenovirus–Based Vectors for Antigen Expression in Animals," *J. Gen. Virol.*, 70:429–434, 1989.

Sager, "Tumor Suppressor Genes: The Puzzle and the Promise," *Science*, 246:1406–1412, Dec. 1989.

Stratford–Perricaudet, "Evaluation of the Transfer and Expression in Mice of an Enzyme–Encoding Gene Using a Human Adenovirus Vector," *Human Gene Therapy*, 1:241–256, 1990.

Stratford–Perricaudet, "Feasibility of Adenovirus–Mediated Gene Transfer In Vivo," *Bone Marrow Transplantation*, 9 (Suppl. 1):151–152, 1992.

Stratford–Perricaudet, "Gene Transfer Into Animals: The Promise of Adenovirus," *Human Gene Transfer*, 219:51–61, 1991.

Stratford–Perricaudet, "Widespread Long–Term Gene Transfer to Mouse Skeletal Muscles and Heart," *J. Clin. Invest.*, 90:626–630, 1992.

Thompson et al., "Gene Expression in oestrogen–dependent human breast cancer xenograft tumours," *British Journal of Cancer*, 62: 78–84, 1990.

Vogelstein et al., "Genetic Alterations Accumulate During Colorectal Tumorigenesis," Negative Controls on Cell Growth, *Journal of Cellular Biochemistry*, USLA Symposia on Molecular and Cellular Biology, 19th Annual Meetings, Feb. 3–Mar. 11, 1990, Abstract #I004, Supplement 14C, 1990.

Watts et al., "Antiestrogen Inhibition of Cell Cycle Progression in Breast Cancer Cells is Associated with Inhibition of Cyclin–Dependent Kinase Activity and Decreased Retinoblastoma Protein Phosphorylation," *MolecularEndocrinology*, 9(12): 1804–1813, 1995.

Weinberg, "Tumor Suppressor Genes," *Science*, 254:1138–1146, 1991.

Wills and Menzel, "Adenovirus Vectors for Gene Therapy of Cancer," *Journal of Cellular Biochemistry*, p. 204, Abstract #S216, Mar.–Apr. 1993.

Zhang and Davis, "Cell–Type Specific Responses in Prostaglandin Secretion by Glandular and Stromal Cells from Pig Endometrium Treated with Catacholestrogens, Methoxyestrogens and Progesterone," *Prostaglandins*, 44: 53–64, 1992.

Zhang and Roth, "Propagation of Recombinant p53 Adenovirus and Evaluation of its Effect on Human Lung Cancer Cells Lines," *The Fourth Meeting on the Molecular Basis of Cancer*, Jun. 1993.

Zhang et al., "Generation and Identification of Recombinant Adenovirus by Liposome–Mediated Transfection and PCR Analysis," *BioTechniques*, 15(5):868–872, 1993.

Zhu et al., "The Carcinogenic Activity of Ethinyl Estrogens is Determined by Both Their Hormonal Characteristics and their Conversion to Catechol Metabolites," *Endocrinology*, 132(2): 577–583, 1993.

Tishler et al., "Microtubule–Active Drugs Taxol, Vinblastine, and Nocodazole Increase the Levels of Transcriptionally Active p53," *Cancer Res.*, 55:6021–6025, 1995.

D'Amato et al., "2–Methoxyestradiol an Endogenous Mammalian Metabolite, Inhibits Tubulin Polymerization by Interacting at the Colchicine Site," *Proceed. Natl. Acad. Sci. USA*, 91:3964–3968, Apr. 1994.

Seegers et al., "The Cytotoxic Effects of Estradiol–17 Beta, Catecholestradiols and Methoxyestradiols in Dividing MCF–7 and HeLa Cells," *J. Steroid Biochem.*, 32(6):797–809, 1989.

Hurd et al., Hormonal Regulation of the p53 Tumor Suppressor Protein in T47D Human Breast Carcinoma Cell Line, *J. Steroid Biochem.*, 270(48):28507–28510, 1995.

Mukhopadhyay et al., Induction of Apoptosis in Human Lung Cancer Cells After Wild–Type p53 Activation by Methoxyestradiol, *Oncogene*, 14(3):379–384, 1997.

International Search Report, Dec. 2, 1997 (INGN:024P—).

* cited by examiner

2-METHOXYESTRADIOL-INDUCED APOPTOSIS IN CANCER CELLS

This is a divisional application Ser. No. 08/688,613 filed Jul. 30, 1996, now U.S. Pat. No. 5,958,892.

BACKGROUND OF THE INVENTION

1. Field of the Invention

The present invention relates generally to the field of cancer therapy. More particularly, it concerns the use of methoxyestradiol to stimulate p53 expression in tumor cells, thereby inducing programmed cell death.

2. Description of Related Art

Normal tissue homeostasis is achieved by an intricate balance between the rate of cell proliferation and the rate of cell death. Disruption of this balance is thought to be a major deleterious event in the development of cancer. The inhibition of apoptosis (programmed cell death) has been linked to this disruptive event. The effects of such defects are catastrophic, causing over half a million deaths per annum in the United States alone.

The p53 gene is well recognized as a tumor suppressor gene (Montenarh, 1992). There is now considerable evidence linking mutations of p53 in the oncogenesis of many human cancers. There are numerous reports demonstrating that the growth of, for example, colon, glioblastoma, breast cancer, osteosarcoma and lung tumor cells can be suppressed by the expression of wild-type p53.

The introduction of wild-type p53 in a wide variety of p53-mutated cells, using viral delivery methods, has resulted in the expression of the wild-type p53 transgene and a suppression of the malignant phenotype. These observations demonstrate that a high level of expression of wild-type p53 is a desirable course for the treatment of oncogenic malignancy.

As the half-life of p53 is very short, ranging between 15 and 20 minutes, it has proved difficult to increase the expression of exogenous p53 using conventional transfection strategies. The microcellular environment of these cells is such that overexpression of wild-type p53 protein, when achieved, is counteracted by rapid degradation. Hence, delivery of wild-type p53 into cancer cells containing wild-type p53 using conventional viral vectors as a way of reducing tumor growth is at best inefficient. A significant percentage of the cancers retain a wild-type p53 gene, but increasing the expression of these genes likely will suffer from the same limitation.

Therefore, there is a clear need for an approach to sustained induction or increase in wild-type p53 expression in cancer cells to mediate apoptosis in such cancer cells.

SUMMARY OF THE INVENTION

It is a goal of the present invention to provide methods for increasing the level of p53 in a target cell. Similarly, it is a goal of the present invention to provide methods for inducing apoptosis in a cell expressing a functional p53. It also is a goal of the present invention to provide improved methods for the treatment of cancers comprising administration of a p53 gene in conjunction with an agent that increase the level of p53 in cells.

In accordance with the present invention, there is provided a method for increasing the level of p53 in a cell having a functional p53 therein, comprising the step of contacting said cell with an amount of 2-methoxyestradiol sufficient to increase the level of p53 in said cell. The p53 may be an endogenous or exogenous protein. The cell may be an endothelial cell or a tumor cell, for example, a lung tumor cell such as a non-small cell lung carcinoma cell.

In another embodiment, there is provided a method for inducing apoptosis in a cell having a transcriptionally active p53 gene therein comprising the step of contacting said cell with an amount of 2-methoxyestradiol sufficient to induce apoptosis in said cell. Again, the p53 gene may be an endogenous or exogenous gene.

In still yet another embodiment, there is provided a method for treating cancer in a patient comprising the steps of (a) determining the p53 status of a tumor cell in said patient; and (b) contacting said tumor cell with an amount of 2-methoxyestradiol sufficient to induce apoptosis in said cell. Where the p53 status of said tumor cell is that it contains a functional p53, further provision of p53 is unnecessary. Where the p53 status of said tumor cell is that it lacks a functional p53 protein, the method further comprises the transfer of a wild-type p53 gene into said tumor cell.

In a particular embodiment, transfer of a p53 gene comprises contacting said tumor cell with an adenovirus containing said wild-type p53 gene. The adenovirus may be replication defective, and in particular, may be lacking at least a portion of the E1 region. Administration of the 2-methoxyestradiol is via intravenous or intratumoral administration.

In still yet another embodiment, there are provided kits for the treatment of cancer using 2-methoxyestradiol.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
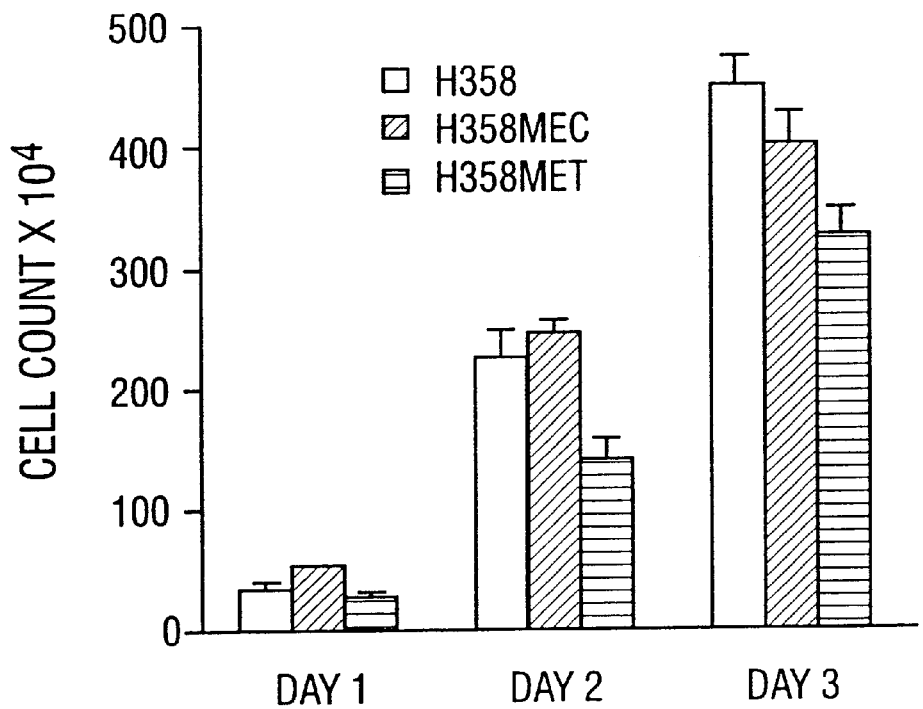
FIG. 1. Cell growth measured in untreated controls or with 5 μm 2-MeOE$_2$ or 5 μm epiestriol treatment of H358, H322, H460 and A549 cell lines. Cultures were harvested at various time points and cell numbers were determined after crystal violet staining. Results are representative of three independent studies; bars, S.D.
Figure 1B:
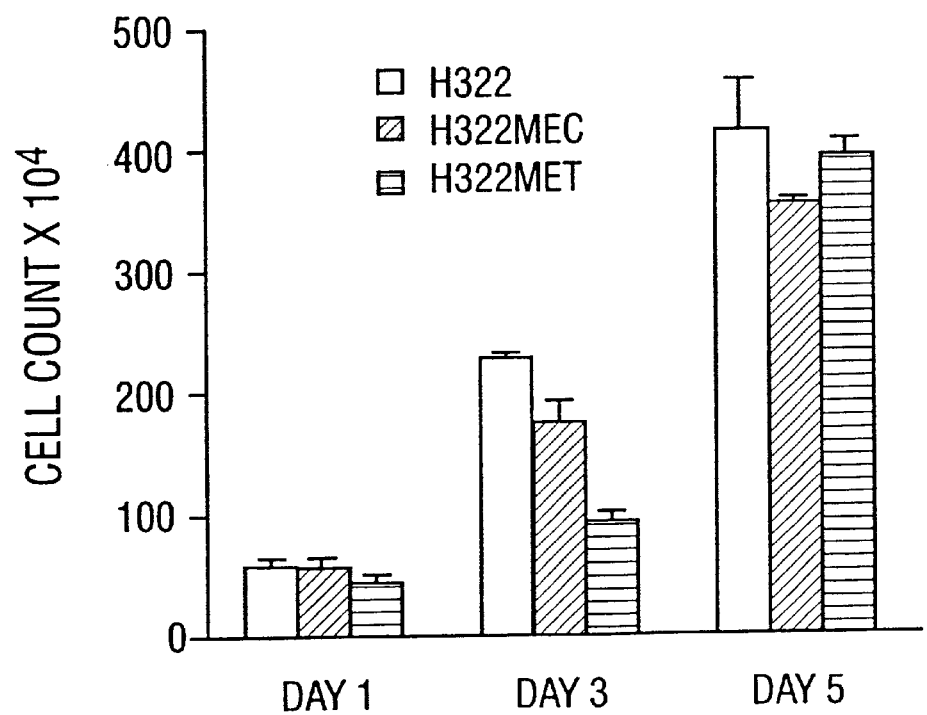
Figure 1C:
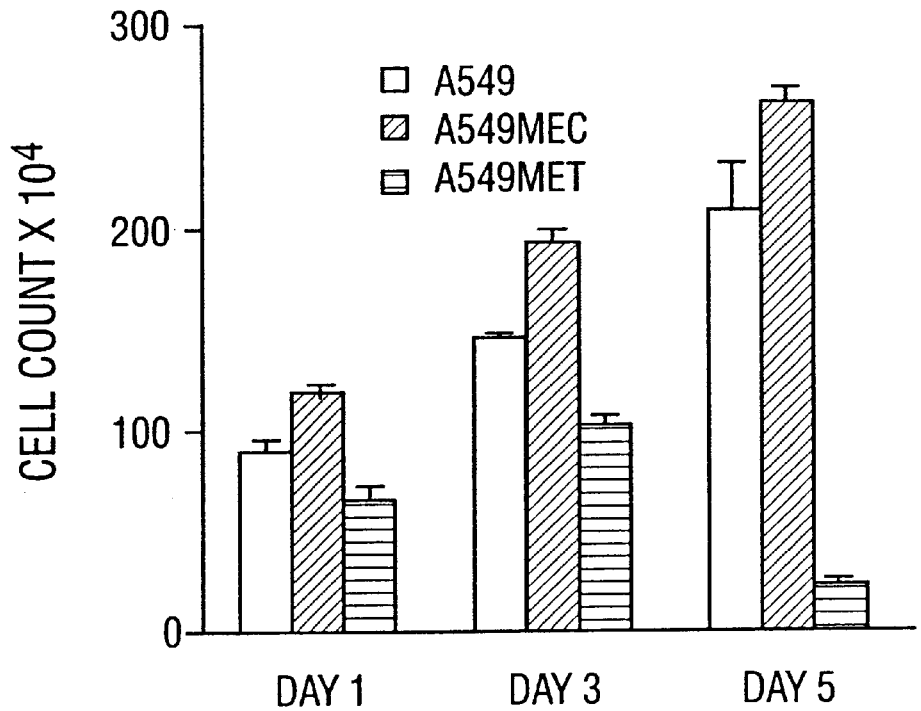
Figure 1D:
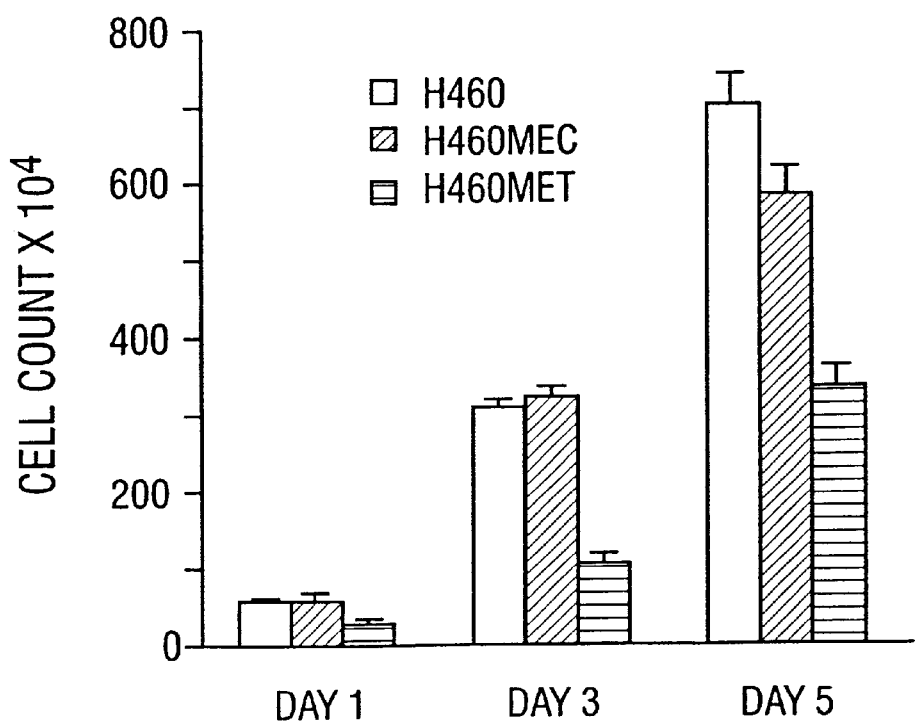

Cancer accounts the death of over half a million people/year in the United States alone. The causes for cancer are multifactorial, however, it is known that aberrations in controlled cell death result in uncontrolled cell proliferation and hence contribute to many cancer. The p53 gene is well recognized as possessing tumor suppressor capabilities and mutations in wild-type p53 are correlated to a variety of cancers.

Many attempts have been made to augment the wild-type p53 expression in tumor cells through gene therapy techniques. These attempts, although potentially valuable, have generally been limited in that the p53 has a very short half life. The present invention provides a means of increasing the level of p53 in tumor cells, thereby allowing for an increased incidence of apoptosis. Wild-type or functional p53 is, and a wild-type or functional p53 gene is one that encodes, defined for the purpose of the present invention, as having tumor suppressing activity. The inventors have discovered that the steroid 2-methoxyestradiol can increase the expression of wild-type p53. This finding can be employed in a number of ways. First, cancers that express normal p53 can be treated with 2-methoxyestradiol as disclosed herein, thereby increasing the levels of p53 and helping to induce apoptosis. Second, the compositions of the present invention can be used to augment conventional gene therapy, where wild-type p53 is introduced into tumor cells. The addition of the 2-methoxyestradiol to the regimen increases the level of p53, inducing or enhancing cell death. A third way in which the present invention is employed is in combination therapy, where gene therapy is used in combination with conventional chemotherapy, and the 2-methoxyestradiol is used to increase wild-type p53 expression thereby inducing programmed cell death.

A. Methoxyestradiol 2-methoxyestradiol (2-MeOE$_2$) is a natural metabolic byproduct of the human body formed by the hydroxylation of estradiol followed by O-methylation in the liver. Some early data indicated that this compound has a cytotoxic effect on the breast cancer cell line MCF-7 (Lottering et al., 1992). The exact mechanism of drag action is not fully understood, but studies have shown that the drug interferes with spindle formation resulting in uneven chromosome distribution, inhibition of DNA synthesis and abnormal metaphases in Chinese Hamster V79 cells in culture (Aizu-Yokota et al., 1995).

In the MCF-7 cell line, 2-MeOE$_2$ has been shown to bind to the colchicine binding site of the tubulin filaments, resulting in either inhibition of tubulin polymerization or alterations in the stability of microtubules, depending on the reaction conditions (Cushman et al., 1995). 2-methoxyestradiol inhibits endothelial cell migration and angiogenesis in vitro (Fotsis et al., 1994).

Interestingly, this compound appears to be non-toxic to normal cells. 2-methoxyestradiol has no effect on normal human skin fibroblasts, even at a 100 $\mu$m concentration, whereas the half-maximal inhibitory concentration of the compound (IC$_{50}$) is 0.15 $\mu$M for endothelial cells (Fotsis et al., 1994). Previous studies have shown that the oral administration of 2-methoxyestradiol in mice results in a potent inhibition of capillary formation in solid tumors and reduced growth. The in vivo studies indicated that the antitumor activity of the 2-MeOE$_2$ was not associated with general cytotoxicity (Fotsis et al., 1994).

Herein, the inventors have demonstrated that 2-MeOE$_2$ increases the level of wild-type p53 in cancer cell lines associated with p21 WAF1/CIP1. The growth inhibition is specific and mediated through p53 induced apoptosis. The effects of 2-MeOE$_2$ treatment on the cell cycle of lung cancer cell lines also was examined. The cell cycle consists of four phases termed G1, S, G2, and M, and the length of time it takes for a cell to go through each phase varies with cell type. For a given cell type, the time to proceed through each phase is relatively constant. However, the timing of the onset of one or more of the phases of the cell cycle can be affected by factors such as nutrient supply and drug treatment. 2-MeOE$_2$ appears to have no effect on the distribution of any of the four phases of the cell cycle in the lung cancer cells lines, as evidenced by flow cytometric analysis. 2-MeOE$_2$ had little inhibitory effect on the p53-negative or p53-mutated cell lines.

B. Assays for Derivatives that Increase Wild-type p53 Expression for Use in the Invention In certain embodiments, the present invention concerns a method for identifying compounds that will increase expression of wild-type p53. It is contemplated that this screening technique will prove useful in the general identification of any compound that will cause an increased p53 expression in cancer cells.

Useful compounds with similar effects on p53 will not be limited to 2-MeOE$_2$. Natural derivatives of estradiol, including but not limited to substitutions of reactive groups at positions in the ring structure of estradiol, may have similar effects on the stabilization of p53. Simple chemical modification of 2-MeOE$_2$ by those skilled in the art, including but not limited to substitution or addition of alkyl, alkoxy, alkenyl, or derivatives thereof, or other groups with small nuclear radii, defined as those elements in the periodic table comprising the first three rows, may have similar effects on p53 expression. These modifications shall include substitution or additions of short unbranched chains containing less than five atoms.

Useful compounds also include fragments or parts of naturally-occurring compounds or may be only found as active combinations of known compounds which are otherwise inactive. Accordingly, in screening assays to identify pharmaceutical agents which increase p53 levels in cancer cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

In these embodiments, the present invention is directed to a method for determining the ability of a candidate substance to increase the wild-type p53 levels in cells, the method including generally the steps of:

(a) obtaining a cell with wild-type p53;

(b) admixing a candidate substance with the cancer cell; and (c) determining the ability of the candidate substance to augment the wild-type p53 content of the cell.

To identify a candidate substance as being capable of increasing p53 levels, one would measure or determine the p53 level of a cell. One would then add the candidate substance to the cell and determine the p53 content in the presence of the candidate substance. A candidate substance which increases the p53 level relative to the p53 level observed in its absence is defined as a candidate substance with positive activity.

"Effective amount," will be defined as that amount effective to reproducibly increase p53 levels in cancer cells when comparison to their control (untreated) levels.

A significant increase in wild-type p53 expression, e.g., as measured using Western blot analysis, is represented by an increase in wild-type p53 levels of at least about 30%–40%, and more preferably, by increases of at least about 50%, with higher values being included. Assays that measure p53 content and expression in cells are well known in the art.

Alternatively, it may be desirable to measure inhibition of growth of cancer cells, for example, by assaying growth according to the MTT assay. A significant inhibition in growth is represented by decreases of at least about 30%–40% as compared to untreated controls, and more preferably, of at least about 50%, with more significant decreases being included. Growth assays as measured by the MTT assay are well known in the art. Assays may be conducted as described by Mosmann et al., 1983; Rubinstein et al., 1990 (incorporated herein by reference). Therefore, if a candidate substance exhibited inhibition of growth of cancer cells in this type of study, it is defined as a compound suitable for use according to the present invention.

Quantitative in vitro testing of the 2-MeOE$_2$ analogs is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context. The skilled artisan is referred to "Remington's Pharmaceutical Sciences" 15th Edition (incorporated herein by reference) for guidance on the use of estrogens generally.

D. p53 and p53 Mutations in Cancer p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild type p53 will reduce the number of malignant cells or their growth rate.

E. Treatment of p53 Positive Cancers using 2-Methoxyestradiol

A patient presenting a tumor that expresses wild-type p53 will be treated with the 2-methoxyestradiol. In such a case, the p53 status of the tumor cells will be determined using any conventional methods, examples of which are described below. Patients may, but need not, have received previous chemo-, radio- or gene therapies. Optimally, patients will have adequate bone marrow function (defined as peripheral absolute granulocyte count of >2,000/mm$^3$ and platelet count of 100,000/mm$^3$), adequate liver function (bilirubin$\leq$1.5 mg/dl) and adequate renal function (creatinine<1.5 mg/dl).

The patient will be treated with a pharmaceutically acceptable form of 2-MeEO$_2$ or a functional analog thereof. This administration could be in the form of, for example, an intratumoral injection, or indeed any other method of application that is routinely used and well know to one of skill in the art, e.g., systemic i.v. A biopsy of the lesions to be injected will be performed and the tissue stored for immunohistochemistry analyses.

The dose of 2-MeOE$_2$ typically will be reconstituted into a pharmaceutically acceptable form immediately prior to administration. The starting dose will be 100 mg/kg body weight 2-MeOE$_2$. Of course this may vary depending on the size of the tumor, the rate at which the tumor is growing, etc. The treatment will be administered over a six week period. During this time, the tumor will be monitored for absence of tumor progression, response or toxicity and the doses adjusted accordingly.

1. Determination of p53 Status of Cells

A wide variety of detection methods can be employed in the present invention to detect the p53 status of a cell. There are numerous antibodies to the p53 protein, hence, any assay that utilizes antibodies for detection, for example, ELISAs, Western Blotting, and other immunoassay techniques, may be used to identify p53 protein. Alternatively, assays that employ nucleotide probes may be used to identify the presence/absence of an intact p53 gene, for example, Southern blotting, Northern blotting or PCR techniques. All the above techniques are well known to one of skill in the art and could be utilized in the present invention without undue experimentation.

i. ELISAs, Immunoassay and Immunohistological Assay

Immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the anti-p53-specific antibodies are immobilized onto a selected surface exhibiting protein affinity, such as a well in a polystyrene microtiter plate. Then, a test composition containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

Variations of ELISA techniques are know to those of skill in the art. In one such variation, the samples containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for the p53 status of the cell also can determine normal/abnormal tissue distribution for diagnostic purposes. Methods for in vitro and in situ analysis are well known and involve assessing binding of antigen-specific antibodies to tissues, cells or cell extracts. These are conventional techniques well within the grasp of those skilled in the art. For example, the antibodies to p53 may be used in conjunction with both fresh-frozen and formalin-fixed, paraffin-embedded tissue blocks prepared for study by immunohistochemistry (IHC). Each tissue block may consist of 50 mg of residual "pulverized" tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990)

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

ii. Southern and Northern Blotting Techniques

Southern and Northern blotting are commonly used techniques in molecular biology and well within the grasp of one skilled in the art.

For Southern blots, the DNA from test cells is recovered by gentle cell rupture in the presence of a cation chelator such as EDTA. The proteins and other cell milieu are removed by admixing with saturated phenol or phenol/chloroform and centrifugation of the emulsion. The DNA is in the upper aqueous phase, it is deprotienised and mixed with ethanol. This solution allows the DNA to precipitate, the DNA can then be recover using centrifugation.

Electrophoresis in agarose or polyacrylamide gels is the most usual way to separate DNA molecules. Southern blotting will confirm the identity of the p53 encoding DNA. This is achieved by transferring the DNA from the intact gel onto nitrocellulose paper. The nitrocellulose paper is then washed in buffer that has for example, a radiolabelled cDNA containing a sequence complementary to wild type-P53 DNA. The probe binds specifically to the DNA that encodes at least a portion of p53 and can be detected using autoradiography by contacting the probed nitrocellulose paper with photographic film.

p53 encoding mRNA can be detected in a similar manner by a process known as Northern blotting. For more detailed description of buffers gel preparation, electrophoresis condition etc. The skilled artisan is referred to Sambrook et al. (1989).

iii. Polymerase Chain Reaction (PCR)

PCR is a powerful tool in modem analytical biology. Short oligonucleotide sequences usually 15–35 bp in length are designed, homologous to flanking regions either side of the sequences to be amplified. Primers are added in excess to the source DNA, in the presence of buffer, enzyme, and free nucleotides. The source DNA is denatured at 95° C. and then cooled to 40–50° C. to allow the primers to anneal. The temperature is adjusted to the optimal temperature for the polymerase for an extension phase. This cycle is repeated 25–40 times.

In particular the present invention uses PCR to detect the p53 status of cells. Mutations in the p53 gene are first detected with Single Strand Conformation Polymorphism (SSCP) which is based on the electrophoretic determination of conformational changes in single stranded DNA molecules induced by point mutations or other forms of slight nucleotide changes. To identify where the mutation is located at within the p53 gene, each exon is separately amplified by PCR using primers specific for the particular exon. After amplification, the PCR product is denatured and separated out on a polyacrylamide gel to detect a shift in mobility due to a conformational change which resulted because of a point mutation or other small nucleotide change in the gene. Mutations result in a change in the physical conformation of the DNA as well as change in the electrical charge of the molecule. Thus, during electrophoresis when an electrical charge is applied to the molecule, DNA that is slightly different in shape and charge as compared to wild type will move at a different rate and thus occupy a different position in the gel.

After determination of which DNA fragment contains the mutation, the specific nucleotide changes are detected by DNA sequencing of the amplified PCR product. Sequencing of linear DNA breaks down the DNA molecule into its individual nucleotides in the order with which they are assembled in the intact molecule. Separation of the individual nucleotides by electrophoresis on a sequencing gel allows detection of individual nucleotide changes compared to wild-type and is used to determine homo- or heterozygocity of a mutation, which is easily distinguished by the appearance of a single or double band in the sequencing gel.

2. Pharmaceutical Compositions and Routes of Administration

Aqueous compositions of the present invention will have an effective amount of a compound that increases the expression of wild-type p53 for example 2-MeOE$_2$. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains a compound or compounds that increase the levels of wild-type p53 will be within the skill of those in the art, in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary, and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

3. Kits

All the essential materials and reagents required for determining wild-type p53 in a sample or for increasing the level of wild-type p53 using 2-MeOE$_2$ in tumor cells may be assembled together in a kit. When the components of the kit are provided in one or more liquid solutions, the liquid solution preferably is an aqueous solution, with a sterile aqueous solution being particularly preferred.

For the detection of wild-type p53, the kit may contain materials for PCR analyses, such primers, buffers and appropriate solvents. Alternatively, if the detection is via immunologic means, the kit may contain antibodies directed to the p53, secondary antibodies that binding primary antibodies, labels or signal generating compounds (either conjugated or unconjugated) and various reagents for the generation and detection of signals.

For in vivo use, a composition, alone or in combination with p53-encoding expression vectors, may be provided. These normally will be separate formulation, but may be formulated into a single pharmaceutically acceptable composition. The container means may itself be geared for administration, such as an inhalant, syringe, pipette, eye dropper, or other such like apparatus, from which the formulation may be applied to an infected area of the body, such as the lungs, injected into an animal, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the agent increasing wild-type p53 expression and/or the gene therapy agents, or explaining the assays for determining p53 levels in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with a separate instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

F. Treatment of Cancers with Mutated p53 Expression using 2-Methoxyestradiol in Combination with Gene Therapy In a separate embodiment of the present invention, it is envisioned that 2-MeOE$_2$ will be used in combination with conventional gene therapy in the treatment of those cancers that express a mutated p53.

It is clear that delivery of wild-type p53 into tumors that express a mutated p53 gene can overcome the deleterious effects of the p53 mutation. In the present embodiment of the invention, 2-methoxyestradiol is administered to the cells along with the wild-type p53 gene thereby increasing the expression of the exogenously applied wild-type p53. The 2-MeOE$_2$ can be administered concurrently with the gene therapy, before the gene therapy or after the gene therapy. All the components of the gene therapy and the therapeutic 2-MeOE$_2$ compositions can be put together in kit form as described above. Elements utilized for gene delivery are described below.

1. Expression Vectors

Throughout this application, the term "expression construct" is meant to include any type of genetic construct containing a nucleic acid coding for a p53 gene product in which part or all of the p53 nucleic acid is capable of being transcribed and subsequently translated into a protein.

In order for the construct to effect expression of a p53 transcript, the polynucleotide encoding the p53 polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module, in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a p53 polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the p53 polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of p53 polynucleotides. Table 1 lists several elements/promoters which may be employed, in the context of the present invention, to regulate the expression of p53 constructs. This list is not intended to be exhaustive of all the possible elements involved in the promotion of p53 expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a p53 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 1

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |

TABLE 1-continued

| ENHANCER |
| --- |
| τ-Globin |
| β-Globin |
| c-fos |
| c-HA-ras |
| Insulin |
| Neural Cell Adhesion Molecule (NCAM) |
| α$_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the p53 construct. For example, with the polynucleotide under the control of the human PAI-1 promoter, expression is inducible by tumor necrosis factor. Table 2 illustrates several promoter/inducer combinations:

TABLE 2

| Element | Inducer |
| --- | --- |
| MT II | Phorbol Ester (TFA) Heavy metals |
| MMTV (mouse mammary tumor virus) | Glucocorticoids |
| B-Interferon | poly(rI)X<br>poly(rc) |
| Adenovirus 5 E2 | E1a |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T.Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding p53. Further examples of selectable markers are well known to one of skill in the art.

One will typically include a polyadenylation signal to effect proper polyadenylation of the transcript. The nature of the polyadenylation signal is not believed to be crucial to the successful practice of the invention, and any such sequence may be employed. Also contemplated as an element of the expression construct is a terminator. These elements can serve to enhance message levels and to minimize read through from the construct into other sequences.

In preferred embodiments of the present invention, the expression construct comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes (discussed below), expression vectors need not be viral but, instead, may be any plasmid, cosmid or phage construct that is capable of supporting expression of encoded genes in mammalian cells, such as pUC or Bluescript™ plasmid series.

i. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed A, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a p53 is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of hepatocytes via asialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

ii. Adenoviruses

Human adenoviruses are double-stranded DNA tumor viruses with genome sizes of approximate 36 kb (Tooze, 1981). As a model system for eukaryotic gene expression, adenoviruses have been widely studied and well characterized, which makes them an attractive system for development of adenovirus as a gene transfer system. This group of viruses is easy to grow and manipulate, and exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991.).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans. The inventor thus reasoned that the characteristics of adenoviruses rendered them good candidates for use in targeting cancer cells in vivo (Grunhaus & Horwitz, 1992).

Particular advantages of an-adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of Adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991). Surprisingly persistent expression of transgenes following adenoviral infection has also been reported.

iii. Other Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viruses offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

2. Alternative Methods for Gene Delivery

In order to effect expression of p53 constructs, the expression vector must be delivered into a cell. As described above, the preferred mechanism for delivery is via viral infection where the expression vector is encapsidated in an infectious adenovirus particle.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, the adenoviral expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an p53 construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a p53 construct may be delivered via this method.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery of p53 construct in many tumor cells that exhibit upregulation of EGF receptor. Galactose can be used to target the asialoglycoprotein receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. During ex vivo culture, the expression vector can express the p53 construct. Finally, the cells may be reintroduced into the original animal, or administered into a distinct animal, in a pharmaceutically acceptable form by any of the means described below.

G. Combination With Standard Chemo- and Radiotherapy

Tumor cell resistance to DNA damaging agents represents a major problem in clinical oncology. One goal of current cancer research is to find ways to improve the efficacy of chemo- and radiotherapy by combining it with gene therapy. In the context of the present invention, it is contemplated that 2-MeOE$_2$ enhanced p53 gene therapy could be used similarly in conjunction with chemo- or radiotherapeutic intervention.

To kill cells, such as malignant or metastatic cells, using the methods and compositions of the present invention, one will contact a "target" cell with 2-MeOE$_2$ and a p53 protein or gene and, optionally, with at least one chemotherapeutic agent, e.g., a DNA damaging agent. These compositions would be provided in a combined amount effective to kill or inhibit proliferation of the cell. This process may involve contacting the cells with the 2-MeOE$_2$ and p53 protein or gene, and the chemotherapeutic agent(s) or factor(s) at the same time. This may be achieved by contacting the cell with a single composition or pharmacological formulation that includes both agents, or by contacting the cell with two distinct compositions or formulations, at the same time, wherein one composition includes the 2-MeOE$_2$ and p53 protein or gene, and the other includes the chemotherapeutic agent.

Alternatively, the 2-MeOE$_2$ enhanced p53 treatment may precede or follow the chemotherapeutic agent treatment by intervals ranging from minutes to weeks. In embodiments where the DNA damaging factor, and 2-MeOE$_2$ and p53 protein or gene are applied separately to the cell, one would generally ensure that a significant period of time did not expire between the time of each delivery, such that the DNA damaging agent and 2-MeOE$_2$ and p53 protein or gene would still be able to exert an advantageously combined effect on the cell. In such instances, it is contemplated that one would contact the cell with both agents within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either 2-MeOE$_2$ and p53 protein or gene, or the chemotherapeutic agent will be desired. Various combinations may be employed, where 2-MeOE$_2$ and p53 protein or gene is "A" and the chemotherapeutic agent is "B":

| A/B/A | B/A/B | B/B/A | A/A/B | A/B/B | B/A/A |
|---|---|---|---|---|---|
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |
| A/B/B/B | B/A/B/B | | | | |

The terms "contacted" and "exposed," when applied to a cell, are used herein to describe the process by which protein, such as 2-MeOE$_2$ and p53, and a chemotherapeutic agent or factor are delivered to a target cell or are placed in direct juxtaposition with the target cell. To achieve cell killing, both agents are delivered to a cell in a combined amount effective to kill the cell.

In particular, the present invention will employ DNA damaging agents as part of a combined therapy protocol. DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with 2-MeOE$_2$ and a p53 protein or gene is particularly preferred as this compound.

Any method also may be used to contact a cell with 2-MeOE$_2$ and p53 protein or gene, so long as the method results in increased levels of functional p53 protein within the cell. This includes both the direct delivery of a p53 protein to the cell and the delivery of a gene or DNA segment that encodes p53, which gene will direct the expression and production of p53 within the cell. In that protein delivery is subject to such drawbacks as protein degradation and low cellular uptake, it is contemplated that the use of a recombinant vector that expresses a p53 protein will provide particular advantages.

In treating cancer according to the invention, one would contact the tumor cells with a chemotherapeutic agent in addition to the 2-MeOE$_2$ and p53 protein or gene. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with 2-MeOE$_2$ and p53 protein or gene, as described above.

Agents that directly cross-link nucleic acids, specifically DNA, are envisaged and are shown herein, to eventuate DNA damage leading to a synergistic anti-neoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis, and chromosomal segregation. Such chemotherapeutic compounds include adriamycin, also known as doxorubicin, etoposide, verapamil, podophyllotoxin, and the like. Widely used in clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of 2-MeOE$_2$ and p53 protein or gene to lung cancer cells in patients with p53-linked cancers will be a very efficient method for delivering a therapeutically effective protein to counteract the clinical disease. Similarly, the chemo- or radiotherapy may be directed to a particular, affected region of the subjects body. Alternatively, systemic delivery of 2-MeOE$_2$ and p53 protein or gene, or the DNA damaging agent may be appropriate in certain circumstances, for example, where extensive metastasis has occurred.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Cell Lines and Tissue Culture

Non-small cell lung cancer cell lines H460 (wild-type p53), H358 (p53 deleted), and pH 322 (p53 mutant) were obtained from Drs. Adi Gazdar and John Minna. A549 (wild-type p53) was obtained from ATCC (Rockville, Md.). All cell lines were grown in RPMI 1640 media supplemented with 5% heat inactivated fetal bovine serum and maintained at 5% CO$_2$. All the studies were done when the cells were 70% confluent.

Western Blot Analysis

Control and drug treated cells were washed in cold PBS, lysed in Laemmli's sample buffer, and subjected to western blot analysis as described previously (Mukhopadhyay et al., 1995). Blots were probed with Pab 1801 anti-p53 monoclonal antibody (Oncogene Sciences, Uniondale, N.Y.). The blot was further probed with anti-WAF1 monoclonal antibody (p21).

Blots were washed in Tris-buffered saline containing 0.1% Tween 20, incubated with horse radish peroxidase conjugated to secondary antibody and specific immunocomplex was detected by enhanced chemiluminescence technique according to the manufacturer's directions (Amersham, Arlington, Ill.). Blots were reprobed with anti-actin monoclonal antibody (Amersham) to show the equal protein loading.

RNA Isolation and Northern Blot Analysis

Total RNA was isolated from the subconfluent cultures using the guanidinium thiocyanate method (Chomczynsky and Sacchi, 1987). Twenty micrograms of total RNA was electrophoresed in 1.4% agarose/MOPS formaldehyde gel, transferred to nylon membrane and hybridized to a radiolabeled p53 cDNA probe as described previously (Mukhopadyay and Roth, 1993).

Analysis of DNA Binding

Electrophoretic mobility shift assays (EMSA) were performed using nuclear extract prepared from the H460 cell line. Nuclear extracts were prepared from untreated control and 2-MeOE$_2$ treated cells. Cells were washed in ice cold PBS and scraped into 0.5 ml nuclei harvesting buffer (10 mM HEPES, pH 7.9; 10 mM KCl; 0.1 mM ETA, 1 mM dithiothretol (DTT), 0.1% NP-40; 0.5 mM phenyl methyl-sulfonyl fluoride; 2 mg/ml leupeptine; 2 mg/ml Aprotinin; 0.5 mg/ml benzamidine). After 30 min of incubation on ice, lysates were centrifuged for 1 min at 4° C. The nuclear pellet was resuspended in nuclear harvesting buffer containing 0.4 M NaCl and incubated on ice for 1 h. The nuclear extracts were microfuged at 12,000 rpm for 30 min at 4° C. and supernatant was stored at −70° C.

To perform electrophoretic mobility shift assays (EMSA), 10 μg of nuclear extract was mixed gently with 0.1 mg of poly (dl-dC) and 1 ng of $^{32}$P-end labeled p53 consensus binding oligonucleotide in binding buffer (25 mM HEPES; pH 7.9; 0.5 mMEDTA; 0.5 mMDTT; 1% NP-40; 5% glycerol; 50 mM NaCl) in total reaction volume 20 μl. One microliter of (1 μg) p53 monoclonal antibody DO1 (Santa Cruz Biotechnology Inc., Calif.) was added to the DNA after binding and incubated for another 15 min to show the supershift. DNA-protein complexes were resolved in native 4.5% polyacrylamide gels.

Growth Assay

For cell growth measurements, $5 \times 10^4$ cells were plated in each well of six well plates. Control and treated cells were trypsinized and counted using a hemocytotometer. Studies were performed in triplicate.

Flow Cytometry Analysis

Control and treated cells were collected by trypsinization, washed in PBS and fixed in 70% ethanol overnight. The next day cells were rehydrated in PBS for 30 min, centrifuged, and resuspended in PBS. For DNA analysis, propidium iodide (Sigma) was added at 50 μg/ml, and the cells were incubated in the presence of RNase at 15 μg/ml for 30 min at 37° C. Flow cytometric analysis was carried out in a fluorescence-activated cell sorter (Coulter Epics Elite).

TdT Staining

Terminal deoxynucleotidyl transferase mediated dUTP-biotin nick end labeling (TUNEL) assay was performed as described previously (Fujiwara et al., 1994). Briefly, the cells were fixed and cytospun on the slide. Cells were incubated in TdT buffer (30 mM Tris Hcl, pH 7.2; 140 mM cacodylate, 1 mM cobalt chloride) and incubated with biotinylated dUTP (Boehringer Mannheim, Indianapolis, Ind.) and 100 U/ml TdT enzyme (Bethesda Research Laboratory) for 1 h at 37° C. The avidin-biotin complex was detected using the Vectastain Elite kit (Vector Laboratory, Burlingame, Calif.), by the diaminobenzidine-H$_2$O$_2$ method.

EXAMPLE II

The Effects of 2-MeOE$_2$ on the Growth Characteristics of Cancer Cells

The inventors tested the effect of 2-MeOE$_2$ treatment on the growth characteristics of four different human lung cancer cell lines differing in their p53 status: H3.58 (p53 deleted), H322 (p53 mutated), H460 (wild-type p53), A549 (wild-type p53).

The cells were treated with 5 μM of 2-MeOE$_2$ or 16-epiestriol (another metabolite of estrogen) and growth of the cells was monitored for five days (FIG. 1).

2-MeOE$_2$ had a significant growth inhibitory effect on the A549 and H460 cells which contain the wild-type p53, whereas it had virtually no growth inhibitory effect on the mutated p53 H322 cell line or on the p53 deleted H358 cell line.

Western blot analysis of the p53 protein after 2-MeOE$_2$ treatment indicated that this drug acted to increase wild-type p53 levels post-transcriptionally when compared with cell lines carrying wild-type p53. The wild-type p53 protein levels are increased 6- to 8-fold during 48 h of 2-MeOE$_2$ treatment in these lung cancer cell lines. However, there was no increase in the level of the mutated p53 protein in the H322 cell line or in normal bronchial epithelial cell lines.

The wild-type p53 manifests its pleiotropic effect by activation of a number of target genes. WAF1 is one of the targets of p53 gene, encodes a p21WAF1/CIP1 protein of 21 kD molecular weight, an inhibitor of cyclin-dependent kinase 2 required for the G1-S transition (El-Deiry et al., 1993). Increased p53 levels after 2-MeOE$_2$ treatment caused activation of the p21 gene. When the blots were reprobed with WAF1 monoclonal antibody, the H460 and A549 cell lines showed 3–5 fold increases in p21 protein expression.

EXAMPLE III

2-MeOE$_2$-Mediated Increase in p53 is Controlled by a Post-Transcriptional Mechanism Dose response studies indicated that in these lung cancer cell lines, 5 µM of 2-MeOE$_2$ treatment stimulated p53 and p21 to a maximum level after 48 h. In order to determine if 2-MeOE$_2$ increased wild-type p53 is predominantly controlled by a post-transcriptional phenomenon, total RNA form H460 control and 48 h after 2-MeOE$_2$ treatment were analyzed by Northern blots.

The blots were probed with radiolabeled p53 cDNA. Results showed no change in the p53 mRNA levels after drug treatment indicating that 2-MeOE$_2$ had no effect on the expression of the wild-type p53 RNA and the level of p53 protein resulted from post-transcriptional modification.

EXAMPLE IV

2-MeOE$_2$ Treatment Results in Increased Expression of p21WAF1/CIP1

Increased p53 protein in H460 cells treated with 2-MeOE$_2$ for 48 h was correlated with increased p53-DNA binding activity. The inventors tested the ability of the p53 protein isolated from control, untreated, and 2MeOE$_2$ treated H460 cell line for its ability to bind to target DNA consensus sequence. H460 cells were treated with 5 µm of 2-MeOE$_2$ for 48 h and then total nuclear extracts was prepared. A three-fold increase in the p53 DNA binding activity was demonstrated in the nuclear extract of 2-MeOE$_2$ treated cells as compared to the untreated control cells. Supershift analysis using anti-p53 monoclonal antibody was done to confirm that p53 protein is binding to the consensus DNA binding elements. These data demonstrate that the wild-type p53 protein produced after 2-MeOE$_2$ treatment is functionally active. Increased p53 expression was associated with increased expression of p21 WAF1/CIP1.

Figure 2A:
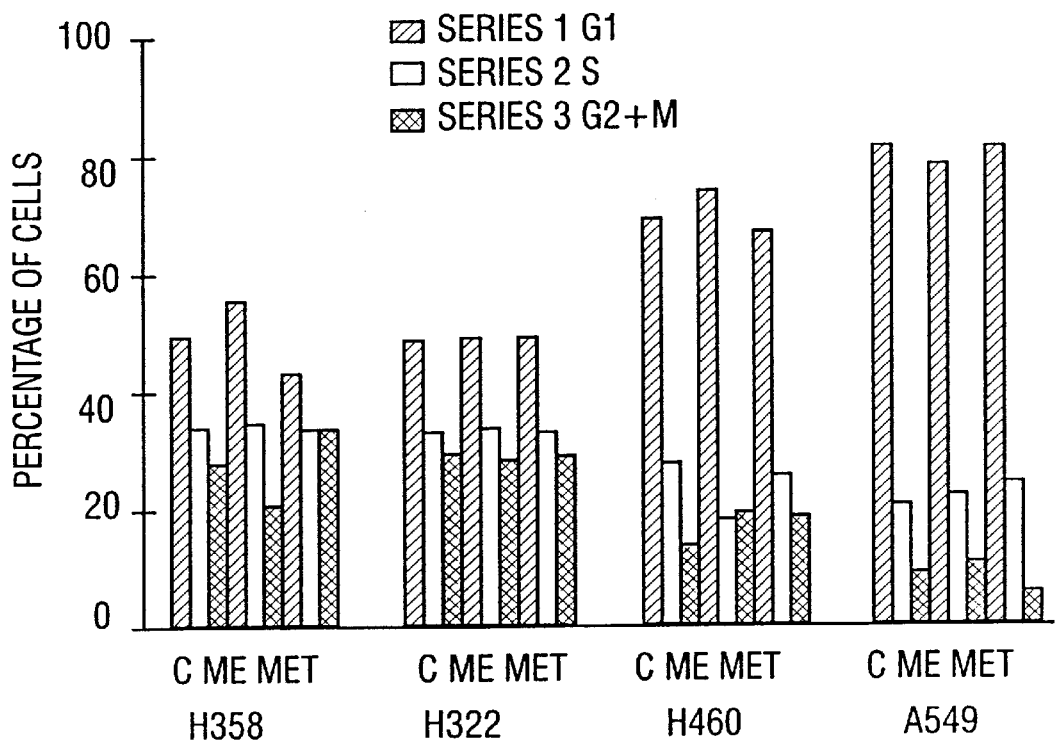
FIG. 2A. Percentage distribution of cells in different cell cycle stages following 48 h of epiestriol (Me) or 2-MeOE$_2$ (Met) treatment. H358 (p53 deleted), H322 (p53 mutated) and H460 (p53 wild-type) cell lines were treated and subjected to cell cycle analysis as described in material and methods and compared with untreated respective control cells (C).

It has been shown that induction of p21 causes p53-mediated G1 arrest and induces apoptosis. However, in these lung cancer cell lines, increase in both wild-type p53 and p21 protein levels had no effect on the cell cycle. Cell cycle analysis indicated no evidence of G1 arrest in these lung cancer cell lines after 2-MeOE$_2$ or epistriol treatment (FIG. 2A). The cells were labeled with PI and cell cycle was analyzed by FACScan. A peak representing apoptotic cells appeared in H460 and A549 cell lines treated with 2-MeOE$_2$. A significant increase in cell death was observed during the growth assay after 48 h of 2-MeOE$_2$ treatment of H460 and A549 cell lines although only two dead cells were noticed in the H322 or in H358 cell lines after crystal violet staining.

Figure 2B:
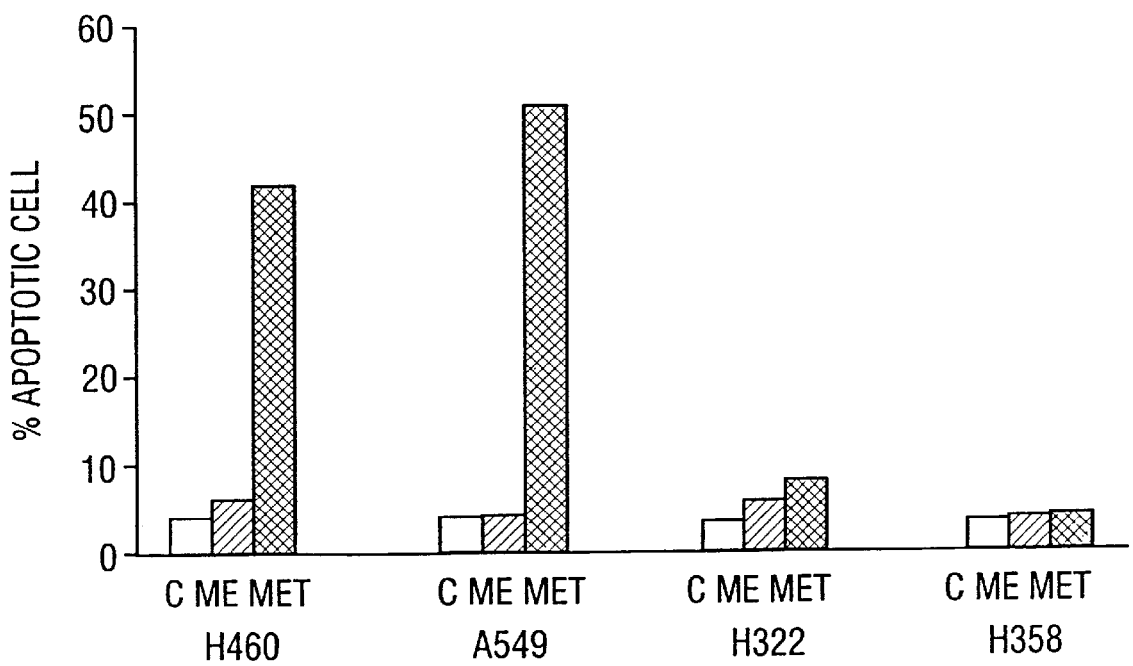
FIG. 2B. Percentage distribution of cells in different cell cycle stages following 48 h of epiestriol (Me) or 2-MeOE$_2$ (Met) treatment. Percentage of cells showing apoptosis was measured by FACScan after staining with UTP-labeled biotin followed by FITC. C, control untreated cell line; Me, cells treated with Epistriol; Met, cells treated with 2-MeOE$_2$.

To confirm that the cells are dying due to apoptosis, both floating and adherent population of cells were pooled and fixed in 70% methanol and concomitantly stained with UTP-labeled biotin followed by FITC-avidin for detection of DNA strand breaks associated with apoptosis. The results indicated that 2-MeOE$_2$ treated H460 and A549 cells had undergone apoptosis. FIG. 2B compares the percentages of apoptotic cells after FACS analysis. A549 cells showed about a 48% apoptotic cell death after 48 h of 5 µm 2-MeOE$_2$ treatment while it had no effect on the 11322 mutated cell lines. Cells also were stained with biotinylated UTP for TUNEL assay to monitor the DNA fragmentation. H460 cells were grown in chamber slides and treated with the drugs and TdT staining was performed as described in Materials and Methods. Cells treated with epistriol or control mock treated cells showed little DNA fragmentation while 2-MeOE$_2$ treated cells displayed many apoptotic bodies. It appears thus apoptosis is specific for these lung cancer cells and dependent on the availability of high levels of wild-type p53 protein in the tumor cells that have already accumulated genetic lesions since the normal bronchial epithelium did not show the observed changes in response to 2-MeOE$_2$ treatment.

The wild-type p53 protein is highly dynamic and undergoes conformational alterations depending on the proliferative state of the cell (Milner and Watson, 1990). With the apparent conformational flexibility of the wild-type p53 protein, pharmacologic intervention might be able to stabilize the protein in a functionally active state. It previously has been shown that Geldanamycin could selectively alter the conformation of mutated p53 and the biochemical properties of the protein (Blagosklony et al., 1995). In the inventors' study, pulse chase studies showed that the half-life of the p53 protein was increased after 2-MeOE$_2$ treatment. Thus post-translational modifications caused by 2-MeOE$_2$ may result in the higher p53 protein levels observed.

These studies clearly demonstrate that 2-MeOE$_2$ increases levels of wild-type p53 gene in a post-transcriptional manner and induces cells to undergo apoptosis. This compound had virtually no effect on p53-mutated or p53-deleted lung cancer cell lines. Thus, this compound is a potent inhibitor of tumor cell growth in cells expressing a wild-type p53 protein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Breast Cancer Res. Treat.,* 16:1 82(#151), 1990.
Allred et al., *Breast Cancer Res. Treat.,* 16:182(#149), 1990.
Anderson et al. U.S. Pat. No. 5,399,346, Mar. 12, 1995.
Aizu-Yokota et al., "Natural Estrogens Induce Modulation of Microtubules in Chinese Hamster V79 Cells in Culture," *Cancer Res.,* 55:1863–1868, 1995.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Benvenisty and Neshif, "Direction introduction of genes into rats and expression of the genes," *Proc. Na'l. Acad. Sci. USA,* 83:9551–9555, 1986.

Blagosklony et al., "Geldanamycin Selectively Destabilizes and Conformationally Alters Mutated p53," *Oncogene,* 11:933–939, 1995.

Brown et al., *Breast Cancer Res. Treat.,* 16:192(#191), 1990.

Boussif et al., "A versatile vector for gene and oligonucleotide transfer into cells in culture and in vivo: Polyethylenimine," *Proc. Nat'l Acad Sci. USA,* 92:7297–7301, 1995.

Casey, et al, "Growth suppression of human breast cancer cells by the introduction of a wild-type p53 gene". *Oncogene,* 6:1791–1797, 1991.

Chang et al., "Foreign gene delivery and expression in hepatocytes using a hepatitis B virus vector," *Hepatology,* 14:124A, 1991.

Chen and Okayama, "High-efficiency transfection of mammalian cells by plasmid DNA," *Mol. Cell Biol.,* 7:2745–2752, 1987.

Chomczynsky and Sacchi, "Methods of RNA Isolation by Acid Guanidinium Thiocyanate-phenol-chloroform Extraction," *Anal. Biochem., 162:156–169, 1987.*

Coffin, "Retroviridae and their replication," In. Fields B N, Knipe D M, ed. Virology. New York: Raven Press, pp. 1437–1500, 1990.

Coupar et al., "A general method for the construction of recombinant vaccinia virus expressing multiple foreign genes," *Gene,* 68:1–10, 1988.

Cushman et al., "Synthesis, Antitubulin and Antimitotic Activity, and Cytotoxicity of Analogs of 2-Methoxyestradiol, and Endogenous Mammalian Metabolite of Estradiol that Inhibits Tubulin Polymerization by Binding to the Colchicine Binding Site," *J. Med. Chem.,* 38:2041–2049, 1995.

Dubensky et al., "Direct transfection of viral and plasmid DNA into the liver or spleen of mice," *Proc. Nat'l Acad. Sci. USA,* 81:7529–7533, 1984.

El-Deiry et al., "WAF1, a Potential Mediator of p53 Tumor Suppression," *Cell,* 75:817–825, 1993.

Fechheimer et al., "Transfection of mammalian cells with plasmid DNA by scrape loading and sonication loading," *Proc. Nat'l Acad. Sci. USA,* 84:8463–8467, 1987.

Ferkol et al., "Regulation of the phosphoenolpyruvate carboxykinase/human factor IX gene introduced into the livers of adult rats by receptor-mediated gene transfer," *FASEB J.,* 7:1081–1091, 1993.

Fotsis et al., "The Endogenous Oestrogen Metabolite 2-Methoxyoestradiol Inhibits Aniogenesis and Suppresses Tumour Growth," *Nature,* 368:237–239, 1994.

Fraley et al., "Entrapment of a bacterial plasmid in phospholipid vesicles: Potential for gene transfer," *Proc. Nat'l Acad. Sci. USA,* 76:3348–3352, 1979.

Friedmann, "Progress toward human gene therapy," *Science,* 244:1275–1281, 1989.

Fujiwara et al., "Induction of Chemosensitivity in Human Lung Cancer Cells by an Adenoviral Wild-Type p53 Expression vector," *Cancer Res.,* 54:2287–2291, 1994.

Ghosh and Bachhawat, "Targeting of liposomes to hepatocytes," In. Wu G, Wu C ed. Liver diseases, targeted diagnosis and therapy using specific receptors and ligands. New York: Marcel Dekker, pp. 87–104, 1991.

Gopal, "Gene transfer method for transient gene expression, stable transfection, and cotransfection of suspension cell cultures," *Mol. Cell Biol.,* 5:1188–1190, 1985.

Graham et al., "Characteristics of a human cell line transformed by DNA from human adenovirus type 5", *J. Gen. Virol.,* 36:59–72, 1977.

Graham and van der Eb, "A new technique for the assay of infectivity of human adenovirus 5 DNA", *Virology,* 52:456–467, 1973.

Grunhaus and Horwitz, "Adenovirus as cloning vector." *Seminar in Virology,* 3:237–252, 1992.

Harland and Weintraub, "Translation of mammalian mRNA injected into Xenopus oocytes is specifically inhibited by antisense RNA," *J. Cell Biol.,* 101:1094–1099, 1985.

Hermonat and Muzycska, "Use of adenoassociated virus as a mammalian DNA cloning vector: Transduction of neomycin resistance into mammalian tissue culture cells," *Proc. Nat'l Acad. Sci. USA,* 81:6466–6470, 1984.

Hollestein, et al., "p53 mutations in human cancers." *Science* 253:49–53 1991.

Horwich, et al., "Synthesis of hepadnavirus particles that contain replication-defective duck hepatitis B virus genomes in cultured HuH7 cells," *J. Virol.,* 64:642–650, 1990.

Kaneda et al., "Increased expression of DNA cointroduced with nuclear protein in adult rat liver," *Science,* 243:375–378, 1989.

Kato et al., "Expression of hepatitis B virus surface antigen in adult rat liver," *J. Biol. Chem.,* 266:3361 –3364, 1991.

Klein et al., "High-velocity microprojectiles for delivering nucleic acids into living cells," *Nature,* 327:70–73, 1987.

Lottering et al., "Effects of 17β-Estradiol Metabolites on Cell Cycle Events in MCF-7 Cells," *Cancer Research,* 52:5926–5932, 1992.

Mann et al., "Construction of a retrovirus packaging mutant and its use to produce helper-free defective retrovirus," *Cell,* 33:153–159, 1983.

Mercer, "Cell cycle regulation and the p53 tumor suppressor protein," *Critic. Rev. Eukar. Gene Express.* 2:251–263, 1992.

Milner and Watson, "Addition of Fresh Medium Induces Cell Cycle and Conformation Changes in p53, a Tumour Suppressor Protein," *Oncogene,* 5:1683–1690, 1990.

Mosmann, "Rapid colorimetric assay for cellular growth and survival: application to proliferation and cytotoxicity assay," *J. Immunol. Methods,* 65:55–63, 1983.

Montenarh, "Biochemical, immunological, and functional aspects of the growth-suppresor/oncoprotein p53," *Crit. Rev. Oncogen,* 3:233–256, 1992.

Mukhopadhyay et al., "Altered Expression of NF-kB P50-Related Proteins is a Common Feature of NSCLC and Tumor-Derived Cell Lines," *Oncogene,* 11:999–1003. 1995.

Mukhopadyay and Roth, "A Codon 248 p53 Mutation Retains Tumor Suppressor Function as Shown by Enhancement of Tumor Growth by Antisense p53," *Cancer Res.,* 53:4362–4366, 1993.

Myers, EPO 0273085

Nicolas and Rubenstein, "Retroviral vectors," In. Rodriguez R L, Denhardt D T, ed. Vectors: A survey of molecular cloning vectors and their uses. Stoneham: Butterworth, pp. 493–513, 1988.

Nicolau and Sene, "Liposome-mediated DNA transfer in eukaryotic cells," *Biochim. Biophys. Acta,* 721:185–190, 1982.

Nicolau et al., "Liposomes as carriers for in vivo gene transfer and expression," *Methods Enzymol.,* 149:157–176, 1987.

Paskind et al., "Dependence of moloney murine leukemia virus production on cell growth," *Virology,* 67:242–248, 1975.

Perales et al., "Gene transfer in vivo: Sustained expression and regulation of genes introduced into the liver by receptor-targeted uptake," *Proc. Nat'l Acad. Sci.* 91:4086–4090, 1994.

Potter et al., "Enhancer-dependent expression of human k immunoglobulin genes introduced into mouse pre-B lymphocytes by electroporation," *Proc. Nat'l Acad. Sci. USA,* 81:7161–7165, 1984.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.,* 10:689–695, 1990.

Roux et al., "A versatile and potentially general approach to the tar ting of specific cell types by retroviruses: Application to the infection of human cells by means of major histocompatibility complex class I and class II antigens by mouse ecotropic murine leukemia virus-derived viruses," *Proc. Nat'l Acad. Sci. USA,* 86:9079–9083, 1989.

Rubinstein et al., "Comparison of in vitro anticancer-drug-screening data generated with a tetrazolium assay versus a protein assay against a diverse panel of human tumor cell lines," *J. Natl. Cancer Inst.,* 82:1113–1120. 1990.

Sambrook et al., Molecular Cloning: A Laboratory Manual, Cold Spring Harbor Press, Cold Spring Harbor. N.Y., 1989.

Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991.

Takahashi et al., "Wild-type but not mutant p53 suppresses the growth of human lung cancer cells bearing multiple genetic lesions," *Cancer Res.* 52:2340–2342, 1992.

Temin, "Retrovirus vectors for gene transfer: Efficient integration into and expression of exogenous DNA in vertebrate cell genome," In. Kucherlapati R, ed. Gene transfer. New York: Plenum Press, pp. 149–188, 1986.

Tooze, "Molecular biology of DNA Tumor viruses", 2nd ed. Cold Spring Harbor Laboratory, Cold Spring Harbor, N.Y., 1991.

Tur-Kaspa et al., "Use of electroporation to introduce biologically active foreign genes into primary rat hepatocytes," *Mol. Cell Biol.,* 6:716–718, 1986.

Wagner et al., *Science,* 260:1510–1513, 1993.

Weinberg, "Tumor suppressor gene". *Science* 254:1138–1145, 1991.

Wong et al., "Appearance of b-lactamase activity in animal cells upon liposome mediated gene transfer," *Gene,* 10:87–94, 1980.

Wu and Wu, *Adv. Drug Delivery Rev.,* 12:159–167, 1993.

Wu and Wu, "Evidence for targeted gene delivery to HepG2 hepatoma cells in vitro," *Biochemistry,* 27:887–892, 1988.

Wu and Wu, "Receptor-mediated in vitro gene transfections by a soluble DNA carrier system," *J. Biol. Chem.,* 262:4429–4432, 1987.

Yang et al., "In vivo and in vitro gene transfer to mammalian somatic cells by particle bombardment," *Proc. Nat'l Acad. Sci. USA,* 87:9568–9572, 1990.

Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 199 1.

What is claimed is:

1. A method for increasing the level of p53 in a human cell in vivo having functional endogenous p53 therein, comprising the step of contacting said cell with an amount of 2-methoxyestradiol sufficient to increase the level of p53 in said cell.

2. The method of claim 1, wherein said cell further contains an exogenous p53 protein.

3. The method of claim 1, wherein said cell is an endothelial cell.

4. The method of claim 1, wherein said cell is a tumor cell.

5. The method of claim 4, wherein said tumor cell is a lung tumor cell.

6. The method of claim 5, wherein said lung tumor cell is an non-small cell lung carcinoma.

7. A method for inducing apoptosis in a human tumor cell having a functional endogenous p53 gene therein comprising the step of contacting said cell in a human cancer subject with an amount of 2-methoxyestradiol sufficient to increase p53 protein level in said cell, thereby inducing apoptosis in said cell.

8. The method of claim 7, wherein said cell is an endothelial cell.

9. The method of claim 7, wherein said cell is a tumor cell.

10. The method of claim 9, wherein said tumor cell is a lung tumor cell.

11. The method of claim 10, wherein said lung tumor cell is a non-small cell lung carcinoma cell.

12. A method for inhibiting tumor growth in a human cancer patient with a tumor comprising the steps of:

(a) determining the p53 status of a tumor cell in said patient, wherein said p53 status indicates that cells of said tumor contain a functional endogenous p53 protein; and (b) administering to said patient an amount of 2-methoxyestradiol sufficient to increase p53 levels in cells of said tumor, thereby inducing apoptosis in cells of said tumor cell.

13. The method of claim 12, wherein said tumor is a lung tumor.

14. The method of claim 13, wherein said lung tumor is a non-small cell lung carcinoma.

15. The method of claim 12, wherein said contacting comprises intravenous administration.

16. The method of claim 12, wherein said contacting comprises intratumoral administration.

17. The method of claim 12, wherein said determining comprises Southern blotting.

18. The method of claim 12, wherein said determining comprises Northern blotting.

19. The method of claim 12, wherein said determining comprises PCR.

20. The method of claim 12, wherein said determining comprises ELISA.

21. The method of claim 12, wherein said determining comprises Western blot.

22. The method of claim 12, wherein said determining comprises immunofluorscence.

23. The method of claim 12, wherein said tumor is a breast cancer.

24. The method of claim 12, wherein said 2-methoxyestradiol is administered more than once.

25. The method of claim 12, wherein said 2-methoxyestradiol is administered at 100 mg/kg.

26. The method of claim 12, wherein said 2-methoxyestradiol is administered over a six week period.

* * * * *